US00PP36548P2

(12) United States Plant Patent
Hansen

(10) Patent No.: US PP36,548 P2
(45) Date of Patent: Mar. 11, 2025

(54) ***EPIMEDIUM* PLANT NAMED 'Cranberry Dancer'**

(50) Latin Name: ***Epimedium* hybrid**
Varietal Denomination: Cranberry Dancer

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,203

(22) Filed: Sep. 13, 2024

(51) Int. Cl.
*A01H 5/02* (2018.01)
*A01H 6/00* (2018.01)

(52) U.S. Cl.
USPC ..... Plt./429
CPC ..... *A01H 6/00* (2018.05)

(58) Field of Classification Search
USPC ..... Plt./429
CPC ..... A01H 5/02
See application file for complete search history.

*Primary Examiner* — Kent L Bell

(57) ABSTRACT

A new cultivar of *Epimedium* plant named 'Cranberry Dancer' characterized by its medium size habit and evergreen foliage with flowers that are burgundy spurs with yellowish tips and prominent burgundy sepals with white margins on airy branched corymbs beginning in mid-spring. The foliage has three leaflets of light chartreuse with bronze coloring in cooler conditions and becoming deep green in summer.

2 Drawing Sheets

Botanical denomination: *Epimedium* hybrid.
Variety designation: 'Cranberry Dancer'.

STATEMENT REGARDING PRIOR DISCLOSURES UNDER 37 CFR 1.77(B)(6)

The Applicant asserts that no publications or advertisements relating to sales, offers for sale, or public distribution occurred more than one year prior to the effective filing date of this application. The first offer for sale was by Walters Gardens, Inc. on Sep. 15, 2023, to Pleasant Run Nursery. Subsequently, on Feb. 1, 2024, a photo and brief description of the new plant was posted on a website hosted by Walters Gardens, Inc. Walters Gardens, Inc. obtained the new plant and all information about the new plant directly from the inventor. Any information or disclosure about the claimed plant less than one year prior to the effective filing date of this application would have been obtained from directly or indirectly from the Inventor and would be a 35 U.S.C. 102(b) exception.

BACKGROUND OF THE INVENTION

The present invention relates to a new and distinct Barrenwort plant from the genus *Epimedium* and given the cultivar name 'Cranberry Dancer'. The new plant was the result of a single seedling selection from a cross on Apr. 30, 2014, by the inventor between 'Amber Queen' U.S. Plant Pat. No. 17,197 as the female or seed parent and the proprietary unnamed selection of *Epimedium zhushanense* (not patented) as the male or pollen parent. The seeds from the pollination were collected in May of 2014. The individually selected seedling was eventually given the breeder code 14-7-2 after being first isolated from trials at a nursery in Zeeland, MI during the April of 2016. It was selected for the final introduction in the April of 2019.

*Epimedium* 'Cranberry Dancer' has been asexually propagated at the same nursery in Zeeland, MI by division of the rhizome in 2016 and found to reproduce plants that are identical and exhibit all the characteristics of the original plant in successive generations of asexual propagation.

*Epimedium* 'Cranberry Dancer', has not been observed under all possible environments. The phenotype may vary slightly with different environmental conditions, such as temperature, light, fertility, moisture and maturity levels, but without any change in the genotype.

In comparison to the new plant, the female parent has smaller flowers of bright yellowish spurs with yellowish sepal. The male parent has a smaller habit with deep purple flower spurs and lavender sepals.

The nearest comparison varieties known to the inventor are: 'Jester's Hat' co-pending U.S. Plant Patent Application No. 63/732,731 and 'Dream Catcher' (Not Patented).

'Jester's Hat' has a similar habit in both height and width but has flowers with brighter golden-yellow spurs with red sepals. 'Dream Catcher' has flowers with light yellow spur tips and reddish sepals.

*Epimedium* 'Cranberry Dancer' is distinct from the parents and all other *Epimedium* known to the inventor in the following combined traits:

1. Medium-sized, dense, evergreen perennial;
2. Large-sized flowers with burgundy spurs with yellowish tips and prominent burgundy sepals with white margins on airy branched panicles beginning in late spring;
3. Foliage has three leaflets, light chartreuse with bronze coloring in cooler conditions becoming medium green in the heat of summer.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
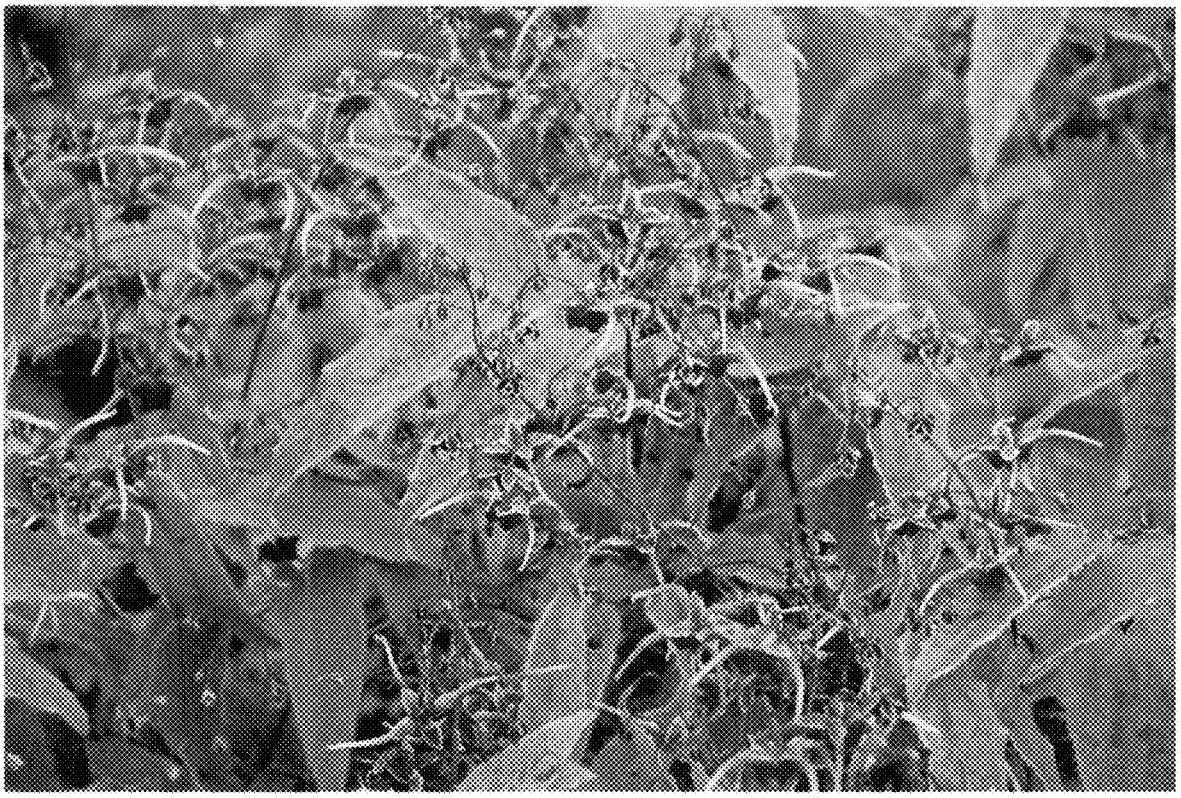
FIG. 1 shows a landscape view of a two-year-old plant in mid-season flower in an overwintered trial block at a nursery near Zeeland, Michigan.
Figure 2:
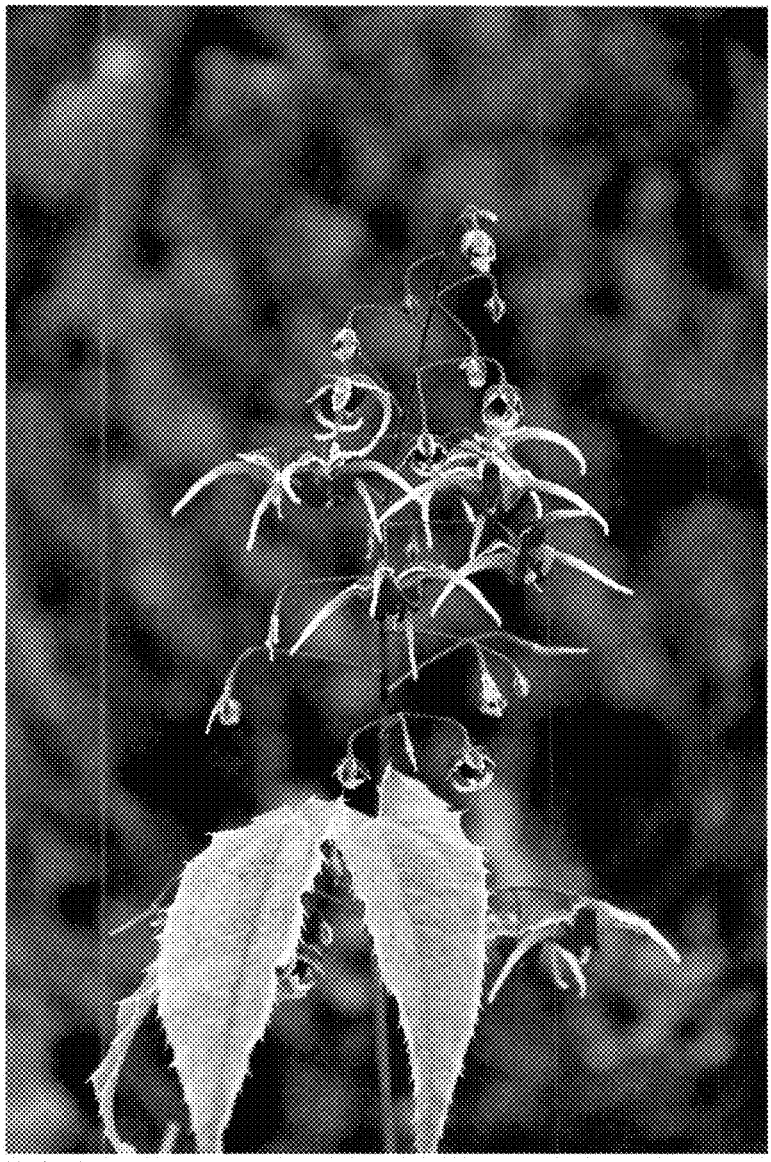
FIG. 2 shows a close-up of the scape.

The following is a detailed description of the new *Epimedium* cultivar 'Cranberry Dancer' based on observations of a two-year-old specimen grown in a shaded greenhouse in Zeeland, Michigan with supplemental watering and fertilizer as needed. Color descriptions are from the 2015 edition of The Royal Horticultural Society Colour Chart except where common dictionary terms are used.

Parentage: The female or seed parent is 'Amber Queen' U.S. Plant Pat. No. 17,197, the male or pollen parent is a proprietary unnamed selection of *Epimedium zhushanense;*

Propagation: Rhizome divisions;

Growth rate: Moderate;

Root development: Initiating in about 6 weeks;

Crop time: Finishing in a 3.8-liter pot from a 50 mm plug in 10 to 12 weeks;

Plant size: Soil level to top of foliar plane to about 44 cm tall and to about 90 cm wide, soil level to top of floral plane about 55 cm;

Root description: Dense, fibrous roots on rhizomes;

Rhizomes: Surface smooth, matte, glabrous; to about 9 cm in length and 5 mm in width; color nearest RHS 147B where exposed to light;

Branching habit: Branches arise from rhizome;

Stem: Cylindrical; moderately glossy, glabrate beginning puberulent; strong; stiff; about 36 cm in length and 2 mm in diameter at base;

Stem color: Variable; older stems between RHS 178B and RHS 177B; young stems between RHS 39C and RHS 186D and between RHS 182C and RHS 185C;

Stem aspect: Initially upright and arching with maturity;

Internode length: 36 cm;

Leaf: Typically one or two tri-parted leaf per node; to 12.5 cm wide and 14.5 cm long;

Leaflet: Three; lanceolate; stiff; acute apex; cordate base slightly overlapping on center leaflet only; slightly undulate; finely serrulate with stiff, sharply-pointed, small spines variably in size from 1 mm to 2 mm wide and 0.5 mm to 3 mm in length; center leaflet to 14 cm long and 5.5 cm wide; side leaflets to 13 cm long and 5.5 cm wide;

Leaflet surface: Adaxial smooth, glabrous, highly lustrous; abaxial smooth, glabrous, matte;

Leaflet color: Young adaxial between RHS 144A and RHS 144B with irregular blotches of nearest RHS 183A, young abaxial between RHS 147C and RHS 146D; mature adaxial nearest NN137B, mature abaxial nearest N138B;

Leaflet venation: Pinnate; adaxial lightly indented; abaxial slightly costate; color adaxial between RHS 147C and RHS 146C, abaxial nearest RHS 146D;

Petioles: Arising from rhizome; cylindrical; smooth; slightly lustrous; stiff; to 36 cm long and 2 mm diameter;

Petiole color: Nearest RHS 146C;

Petiolules: Cylindrical; smooth; slightly lustrous; stiff; to about 3 cm long and 1 mm diameter on center leaflets and to about 2.5 cm long and 0.7 mm diameter on side leaflets;

Petiolule color: Emerging foliage between RHS 146D and RHS N144A maturing to nearest RHS 176A;

Inflorescence: Compound corymb; flowering in the upper 30 cm and to about 21 cm wide; with about 22 branches, branches having to about 11 flowers; inflorescence with about 85 to 100 flowers;

Flower buds one day prior to starting to open: Globose; smooth, glabrous, about 5 mm long and 4 mm diameter;

Bud color one day prior to starting to open: Inner sepals nearest RHS N79B in the longitudinal center and the margins nearest RHS NN155C, outer sepals nearest RHS 79A in longitudinal center and margins nearest RHS NN155C;

Flower: Perfect; complete; actinomorphic;

Flower size: To about 44 mm in diameter and 18 mm in depth;

Flower fragrance: None detected;

Lastingness of flowers: About 7 days from initial opening dehiscence; self-cleaning;

Petals: Four; spurs; lanceolate; arcuate outwardly and curving toward center axis; apex narrowly acute; base truncate, adnate on axial portion; adaxial and abaxial smooth, glabrous and slightly lustrous; to about 19 mm long natural, 26 mm long straightened, and about 7 mm across at opening;

Petal color: When opening and fully open spur adaxial and abaxial proximally between RHS 187C and RHS 187B, with distal 5 mm nearest RHS 14D, and the apical 1 mm nearest RHS 20A;

Pedicel: Cylindrical; puberulent to micro-glandular; to about 18 mm long and 0.3 mm diameter; average about 10 mm long and 0.3 mm diameter at base;

Pedicel color: Nearest RHS N186C proximally and distally nearest RHS N144C;

Peduncle: Cylindrical; stiff; strong; glabrous; slightly lustrous; with to about 22 branches; main peduncle aspect upright to arching, branches outwardly to nearly 90 degrees from main axis; to about 28 cm long and 2 mm diameter at base; branches to about 7 cm long and 1 mm diameter at base;

Peduncle color: Proximal portion nearest RHS 146D moderately to heavily maculate with nearest RHS 183C, distal portion between RHS 146C and RHS 146B, with branch nodes between RHS 147B and RHS 146A;

Sepals: Four; rotate; single whorl; hyaline; ovate; smooth, glabrous and matte; attenuate base, acute apex; margin entire; to about 11 mm long and 6 mm across;

Sepal color: Adaxial and abaxial proximal longitudinal center heavily maculate between RHS N79B and RHS N79C, distal longitudinal center nearest RHS 76B and margins nearest RHS NN155D;

Androecium: Four;

*Anther*.—Four; longitudinal; basifixed; extrose; oblong; to about 3 mm long and 1 mm across; color prior to opening nearest RHS 8B.

*Filaments*.—Four; applanate; about 3.5 mm long and 1 mm wide at base, narrowing distally; color nearest RHS 7B.

*Pollen*.—Abundant; color nearest RHS 12A.

Gynoecium: Single; superior;

*Style*.—Cylindrical; glabrous; about 2.5 mm long and 0.3 mm diameter; color nearest RHS 145C.

*Stigma*.—Oblong; glabrous; to about.05 mm long and about 0.5 mm diameter; color nearest RHS 145C.

*Ovary*.—Oblong; glabrous; smooth; to about 3 mm long and 0.8 mm diameter; color nearest RHS 145A.

Fruit/seeds: None observed to date.

Resistance: Not been tested or shown to be susceptible or resistance to pests and diseases common to *Epimedium;*

Hardiness: The new plant has survived USDA winter hardiness to at least zones 5 to 8 but has not been tested yet beyond these temperatures.

It is claimed:

1. A new and distinct cultivar of *Epimedium* plant named 'Cranberry Dancer' as herein described and illustrated.

* * * * *